US006842218B1

(12) United States Patent
Manne

(10) Patent No.: US 6,842,218 B1
(45) Date of Patent: Jan. 11, 2005

(54) SCENT DELIVERY SYSTEM

(76) Inventor: Joseph Manne, 920 Park Ave., New York, NY (US) 10028-0208

( * ) Notice: Subject to any disclaimer, the term of this patent is extended or adjusted under 35 U.S.C. 154(b) by 0 days.

(21) Appl. No.: 10/627,054

(22) Filed: Jul. 25, 2003

Related U.S. Application Data

(60) Provisional application No. 60/399,248, filed on Jul. 29, 2002.

(51) Int. Cl.[7] .......................... G03B 21/32; F02M 69/02

(52) U.S. Cl. ........................................... 352/85; 261/30

(58) Field of Search .............................. 352/85; 261/24, 261/30, 141; 348/460

(56) References Cited

U.S. PATENT DOCUMENTS

| | | | | |
|---|---|---|---|---|
| 2,540,144 A | * | 2/1951 | Stern | 348/460 |
| 5,610,674 A | * | 3/1997 | Martin | 352/85 |
| 5,898,475 A | * | 4/1999 | Martin | 352/85 |
| 5,949,522 A | * | 9/1999 | Manne | 352/85 |

* cited by examiner

*Primary Examiner*—Judy Nguyen
*Assistant Examiner*—Arthur A Smith
(74) *Attorney, Agent, or Firm*—Muserlian, Lucas & Mercanti

(57) ABSTRACT

The scent delivery system employs a single conduit with a nasal interface at one end and a fan or canister of compressed air at the other end. In between the two ends a scent injection device is positioned. The injection device injects scent into an air flow created by the fan or canister and creates scented air which is carried to the nose by the flow of air.

13 Claims, 5 Drawing Sheets

SCENT DELIVERY SYSTEM

CROSS-REFERENCE TO RELATED APPLICATIONS

This application claims the priority under 35 USC 119(e) of U.S. provisional patent application Ser. No. 60/399,248 filed Jul. 29, 2002.

BACKGROUND OF THE INVENTION

1. Field of the Invention

The present invention relates to a scent delivery system for air flowing in a conduit and, more particularly, to a scent delivery system which can be used with a portable system as well as a multi-media device.

2. Art Relating to the Invention

There are numerous scent delivery systems which have been used with multi-media devices. For example, see U.S. Pat. No. 5,949,522 and International patent application No. PCT/US98/13986. The '522 patent illustrates a non-portable system while the International application '986 illustrates a portable arrangement, both of which add scented air at one end of a conduit and convey that scented air to a nasal interface at the other end of the conduit.

SUMMARY OF THE INVENTION

A scent delivery system has now been invented which is especially suited for use as both a portable system and with multi-media systems that add scent to air already flowing in a conduit. The system of the present invention employs a single conduit with a means for injecting scent into the conduit. A nasal interface is connected to one end of the conduit while a means for creating a flow of air in the conduit is connected to the other end of the conduit. The means for injecting scent into the conduit is positioned along the side of the conduit, in between the two ends. The system of the present invention is both simple and inexpensive to manufacture.

The present invention can be used to deliver one scent or a plurality of scents to a user's nose.

Broadly, the present invention may be defined as a scented air delivery device which comprises:

(a) a conduit having two open ends and at least one side opening in a side wall of said conduit;

(b) a nasal interface affixed to one of said open ends of said conduit, said nasal interface adapted for wearing in close proximity to a nasal cavity of a user;

(c) a means for creating an air flow affixed to the other of said open ends of said conduit, said means for creating an air flow forces air from said other of said open ends of said conduit to said one of said open ends of said conduit and into said nasal interface; and (d) means for injecting scent into said air flow through said side opening in said conduit, said injection means affixed to a side of said conduit at said side opening so as to inject scent into said air flow and create scented air in said conduit.

Suitably, the nasal interface is a nose mask, a face mask, a tee, a wishbone or an outlet in said conduit.

Suitably, the means for creating an air flow is a fan blower, a canister of compressed air, or any conventional means to create an air flow.

Suitably, the means for injecting scent into the conduit is a plurality of scent reservoirs and said conduit has a plurality of side openings, said reservoirs affixed to the side of said conduit one at each of said side openings, each reservoir having a means to inject scent into air in said conduit.

Alternatively, the means for injecting scent into the conduit comprises:

(a) a frame affixed to said conduit at said side opening;

(b) a rotatable wheel affixed to said frame, said wheel having an axis of rotation parallel to an axis of said conduit;

(c) one or more scent containers affixed to said wheel, each of said containers having (i) an outer elongated sleeve affixed to said wheel, one end of said outer sleeve being open and adjacent to a rim of said wheel, another end of said outer sleeve facing said axis of said wheel, (ii) a scent reservoir having an outlet, (iii) an inner sleeve concentric with, positioned in, and movable in said outer sleeve, one end of said inner sleeve being closed and facing said rim of said wheel, another end of said inner sleeve extending into said reservoir through said outlet of said reservoir and affixed to said reservoir at said outlet, (iv) at least one window in a side wall of said inner sleeve, said window positioned adjacent said one end of said inner sleeve, (v) a wick positioned in said inner sleeve and extending from said scent reservoir to said window, (d) means for moving said inner sleeve and said reservoir to open and close said window such that, when said window is open, said inner sleeve is in said conduit and said window allows scent from said wick to enter said air flow in said conduit and, when said window is closed, said inner sleeve is outside said conduit and said window is against an inside wall of said outer sleeve so as to prevent scent from entering said air flow;

(e) a motor for rotating said wheel to align each of said inner sleeve of said scent containers with said side opening to allow scent from said scent reservoir to be delivered to an air flow in said conduit.

Suitably, the means for moving the inner sleeve is a solenoid with an associated arm which can raise the inner sleeve up and into the conduit. A source of electricity is employed to activate the solenoid while a spring is affixed between the reservoir and the outer sleeve such that when the solenoid is deactivated, or the power turned off, the spring will force the inner sleeve out of engagement with the conduit, likewise forcing the arm of the solenoid downward.

Alternatively, the means for moving the inner sleeve is a cam and a spring. The cam is situated such that as the wheel rotates and brings a scent container into alignment with the conduit, the reservoir rides over the cam and is forced upward, thereby forcing the inner sleeve upward and into the conduit. A spring is mounted between the outer sleeve and the reservoir such that, as the wheel rotates, the reservoir comes off the cam and the spring forces the reservoir downward, thereby forcing the inner sleeve downward.

Alternatively, a motor with an eccentric gear can be employed so as to move the reservoir and inner sleeve upward when the inner sleeve is positioned below the conduit. By activating the motor in reverse, the inner sleeve is drawn downward. In this embodiment, a spring is also employed between the outer sleeve and the reservoir in order to ensure that the window stays closed as the wheel rotates.

Additionally, multiple wheels can be used with one conduit so as to increase the number of containers which are available to that conduit or, alternatively, to allow for mixing of scent in the same conduit.

Suitably, the system of the present invention is portable.

BRIEF DESCRIPTION OF THE DRAWINGS

These and other aspects of the present invention may be more fully understood by reference to one or more of the following drawings wherein.

DETAILED DESCRIPTION OF THE INVENTION

Figure 1:
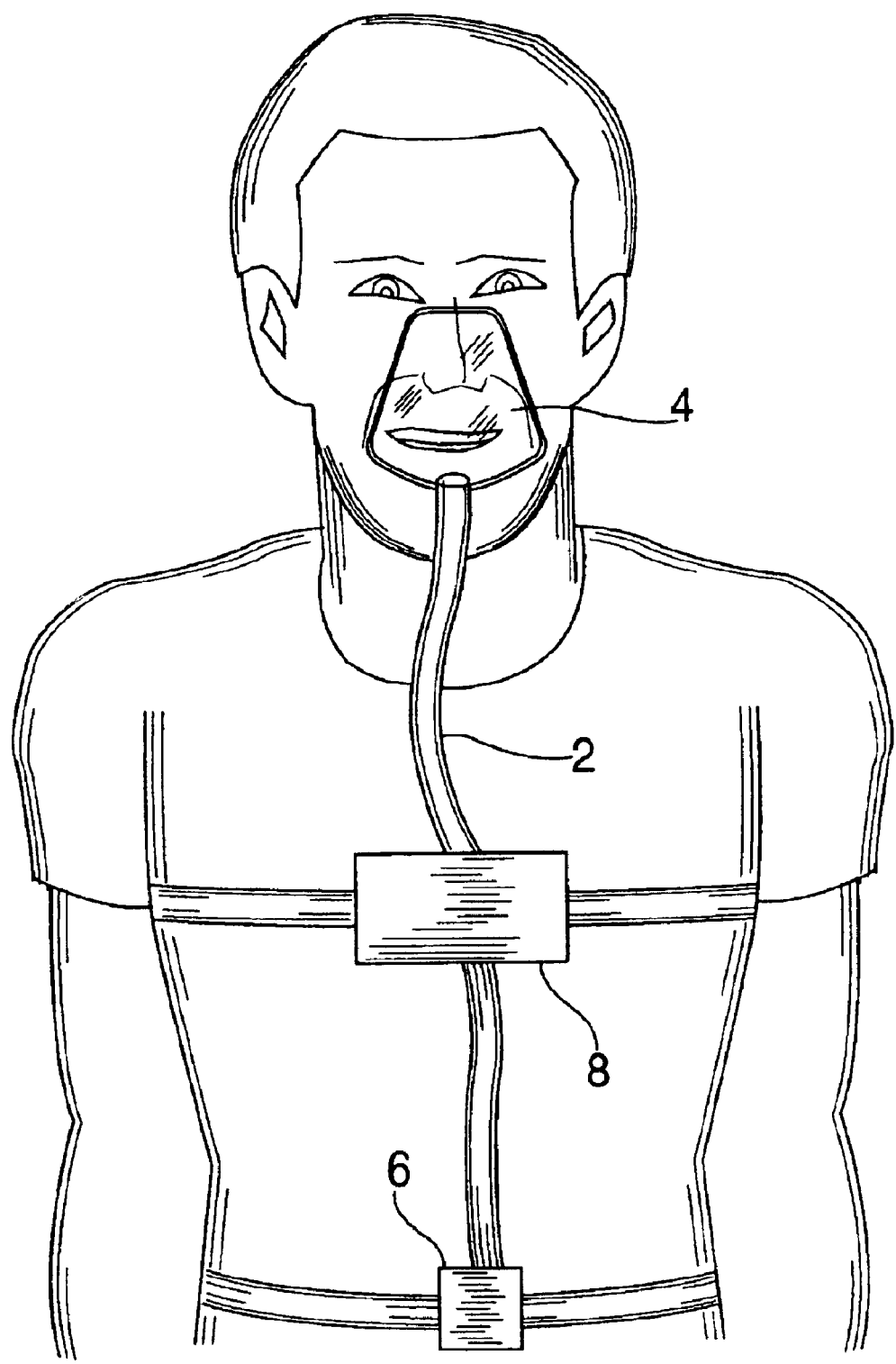
FIG. 1 is an over view of the present invention.

As shown in FIG. 1, the present invention has conduit 2 with one end attached to nasal interface 4 and the other end attached to means 6 for creating an air flow in conduit 2. Affixed to a side wall of conduit 2 is means 8 for injecting scent into the air flow in conduit 2.

Figure 2:
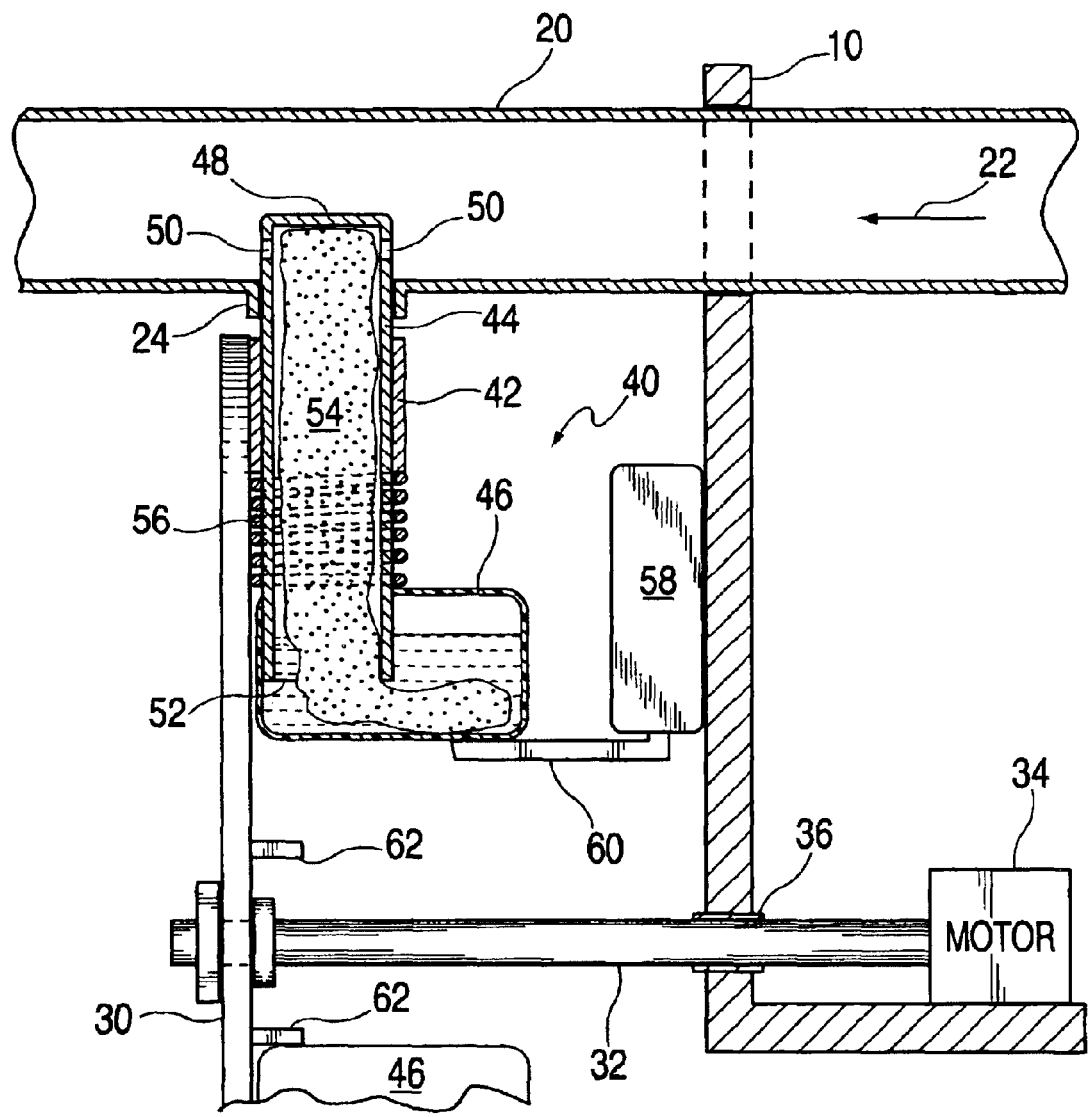
FIG. 2 is a side view of the means for injecting scent of the present invention.

As shown in FIG. 2, frame 10 is attached to conduit 20 in which air flow 22 moves. In the side wall of conduit 20 is inlet 24. Inlet 24 can have side walls as shown in FIG. 2 to assist in the registration and insertion of the inner conduit as discussed herein.

Frame 10 holds wheel 30 by means of axle 32. Axle 32 is connected to motor 34. Motor 34 is any suitable electric motor that can rotate wheel 30 upon command. Motor 30 can be connected to a CPU unit or other processor (not shown) which would allow for accurate rotation and stopping of wheel 30. The purpose of accurate rotation is to allow motor 34 to rotate wheel 30 and register various scent containers 40 under hole 24 of conduit 20. Bushing 36 in frame 10 allows for rotation of axle 32.

Figure 3:
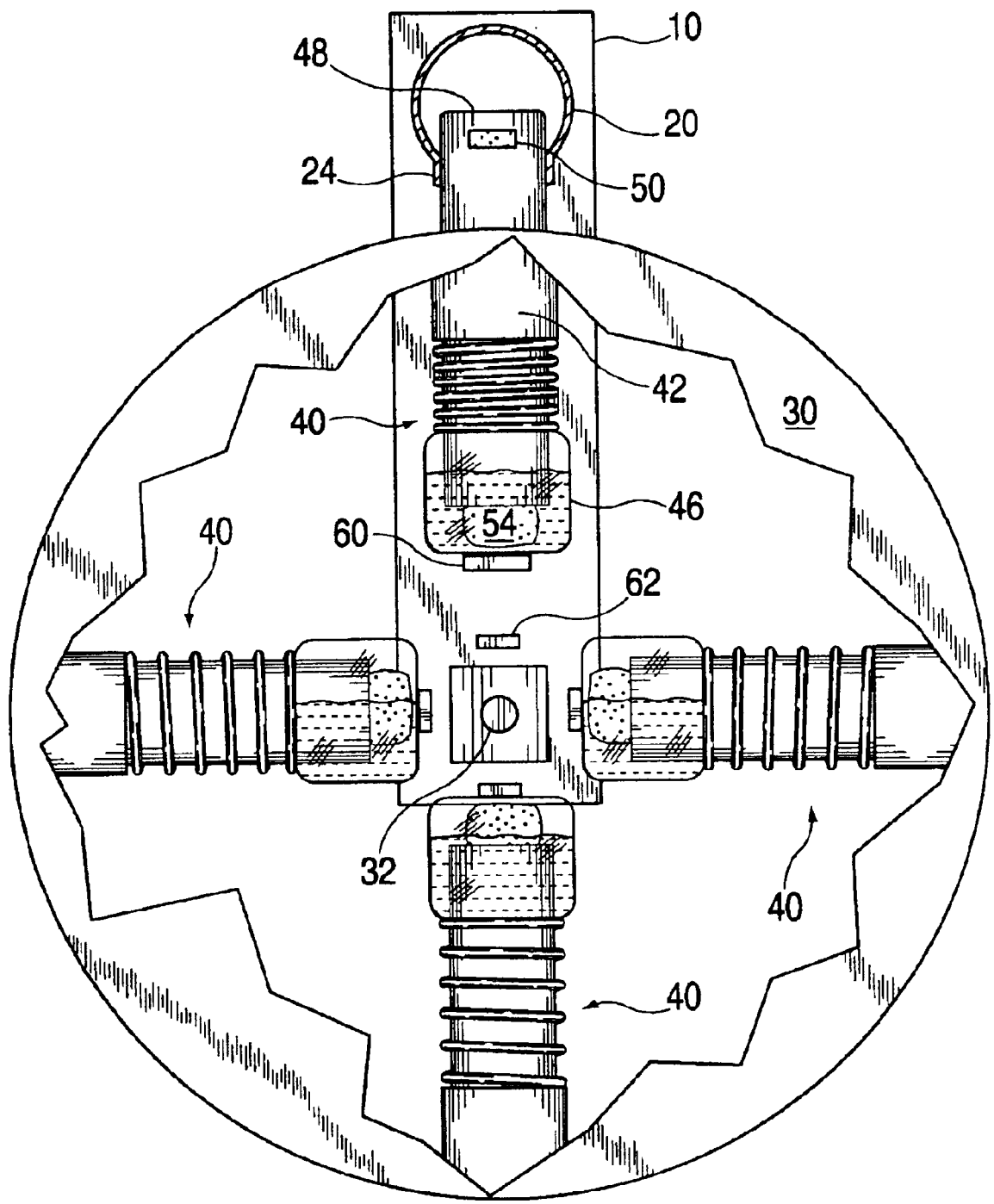
FIG. 3 is a front view of the means of FIG. 2.

As shown in FIG. 3, a plurality of scent containers 40 are affixed to wheel 30.

Scent containers 40 each comprise outer sleeve 42 which is permanently affixed to wheel 30, inner sleeve 44 which is permanently affixed to reservoir 46. Inner sleeve 44 and reservoir 46 are affixed to each other such that, as inner sleeve 44 moves inside of outer sleeve 42, scent reservoir 46 moves with inner sleeve 44. Outer sleeve 42 has both ends open with one end affixed at the rim of wheel 30 and the other end facing towards axle 32. By having both ends open, outer sleeve 42 allows for up and down movement of inner sleeve 44. As will be appreciated, the outer diameter of inner sleeve 44 corresponds with the inner diameter of outer sleeve 42 to allow for inner sleeve 44 to move within outer sleeve 42 while maintaining a tight engagement. This tight engagement is important for purposes of preventing loss of scent when inner sleeve 44 is in a down position.

Inner sleeve 44 has closed top 48, window 50 and open bottom 52. Wick 54 is positioned in inner sleeve 44 and extends from closed top 48 through open bottom 52 and into scent reservoir 46.

Open bottom 52 is positioned near the bottom of reservoir 46 to minimize the amount of scent liquid which is housed within reservoir 46 from flowing down inner sleeve 44 when the scent container 40 is upside down. Wick 54 is intended to essentially block and fill all of the inside cavity of inner sleeve 44 and to be able to absorb and carry through capillary action scented liquid from reservoir 46 up through inner sleeve 44 and to window 50.

When window 50 is positioned within conduit 20 as shown in FIG. 2, air flow 22 picks up scent from wick 54 as the air passes through and around window 50. In this manner, air flow 22 becomes scented.

Figure 4:
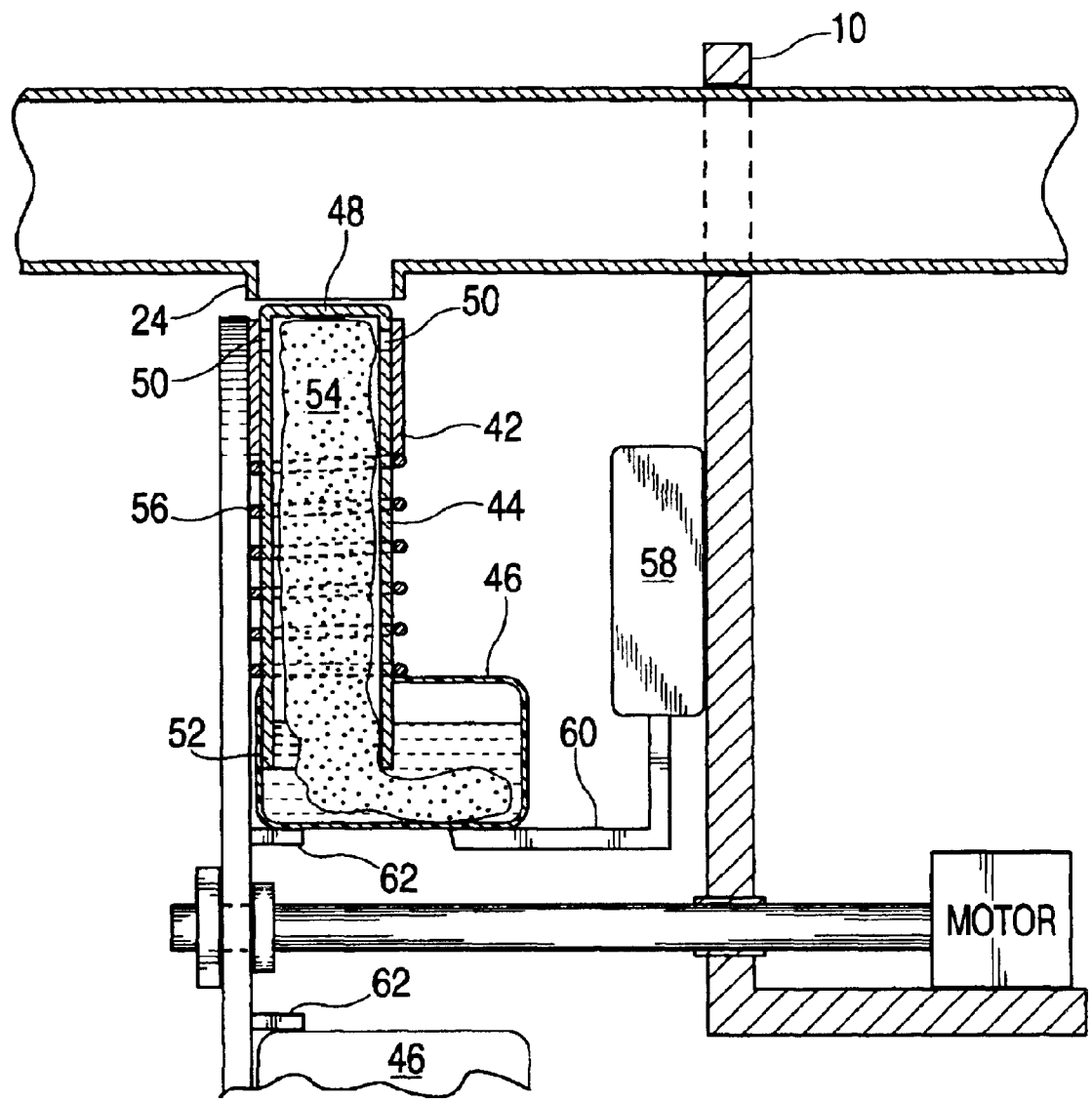
FIG. 4 is a side view of the means of FIG. 2 wherein the inner sleeve is not in engagement with the conduit.

When inner sleeve 44 is lowered as shown in FIG. 4, window 50 is closed due to its tight engagement with the inner wall of outer sleeve 42.

Inner sleeve 44 and scent reservoir 46 move together since they are affixed to one another. In order to move inner sleeve 44 and scent reservoir 46, spring 56 which is shown as a coil spring in the FIGS. 2-4, is positioned between outer sleeve 42 and reservoir 46. Spring 56 pushes reservoir 46 downward. In order to move reservoir 46 and inner sleeve 44 upward, solenoid 58 has arm 60. Solenoid 58 is affixed to frame 10. In order to push inner sleeve 44 and reservoir 46 upward, solenoid 58 is activated to force arm 60 to raise inner sleeve 44 and reservoir 46. When solenoid 58 is deactivated, spring 56 pushes reservoir 46 downward until the bottom of reservoir 46 engages stop 62.

Solenoid 58 and arm 60 can be replaced by a conventional cam affixed to frame 10 in a conventional manner and positioned so as to force reservoir 46 and inner sleeve 44 upward as the bottom of reservoir 46 engages the cam and comes into registration with opening 24.

Alternatively, solenoid 58 and arm 60 can be replaced with a motor with an eccentric gear thereon affixed to frame 10. The eccentric gear would engage the bottom of reservoir 46 and allow the motor to drive the reservoir 46 upward when engaged. The motor would then be reversed in order to lower reservoir 46 and inner sleeve 44. In this arrangement, spring 56 would still be employed so as to maintain window 50 in a closed position when scent container 40 is upside down as shown in FIG. 3.

In FIG. 3, four different scent containers 40 are illustrated. As will be appreciated by one of skill in the art, a plurality of scent containers can be positioned around wheel 30. The number of scent containers 40 which can be positioned around wheel 30 depends upon the size of the wheel 30 and the size of scent containers 40.

Also, as will be appreciated by those of skill in the art, a plurality of frames with the associated wheel and scent containers can be positioned along conduit 20. This arrangement would increase the number of scent containers that are available to the conduit and its associated air flow and/or allow for mixing of scents. In other words, if there were two wheels, each with their own scent containers, both wheels could have scent containers registered with two separate holes in the conduit and both of those scent containers could be activated so that their windows were open within the air flow of the conduit. This would allow two scents to be added to the air flow and thus a mixing of scents in the air flow to allow a mixture of scents to be delivered to the user's nose.

Scent reservoir 46 preferably employs a liquid which has a scent. The term "scent" as used in the specification and claims means an effluvia that affects the sense of smell. The substance is preferably a liquid which fills scent reservoir 46. Naturally, this liquid could also be a gel provided that the substance, or at least its scent, can travel up or through wick 54 to arrive at window 50.

The term "wick" has been used to infer the capillary type action of a liquid upward through inner sleeve 44. However, any type of packing material can be used. The purpose of the packing material is to prevent the loss of the liquid from scent reservoir 46. Naturally, if a gel were employed and the gel had low flow characteristics, it is possible that inner sleeve 44 would not need to extend down and into scent reservoir 46.

Figure 5:
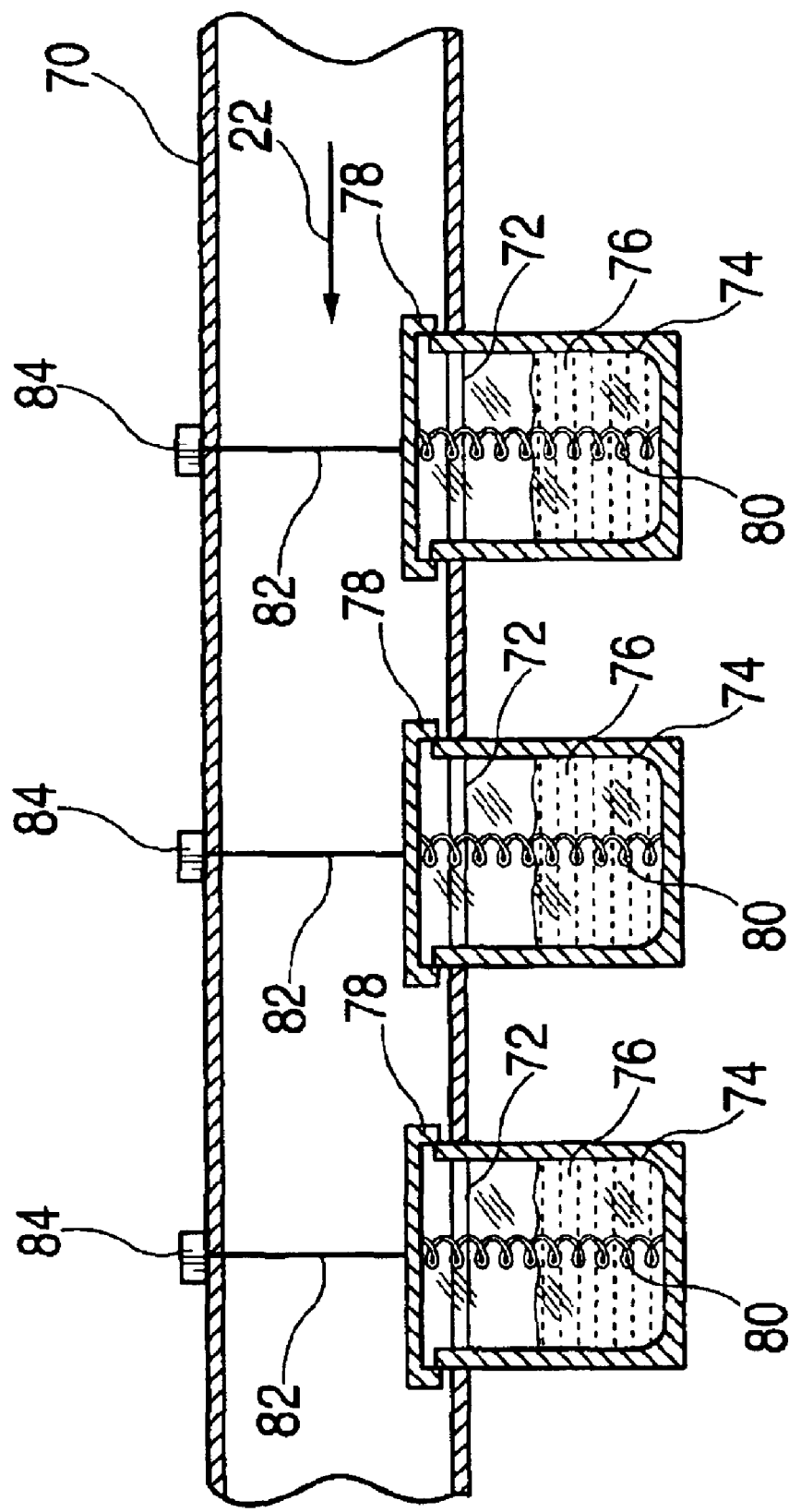
FIG. 5 is another embodiment of the means for injecting scent into the conduit in accordance with the present invention.

FIG. 5 illustrates yet another embodiment of the means for injecting scent into the air flow. Conduit 70 has air flow 22 therein. Conduit 70 has a plurality of inlets 72 and a plurality of scent reservoirs 74 each of which are affixed to the side of conduit 70. Each reservoir 74 is filled with a gel 76 that can release scent. Each reservoir 74 has cap 78 which is held against the top of reservoir 74 by coil spring 80. Dynamic alloy wire 82 is attached to the outside of cap 78 and has electrical connection 84 which can activate dynamic alloy wire 82 thereby lifting cap 78 and releasing scent into air flow 22.

It will be understood that the claims are intended to cover all changes and modifications of the preferred embodiments of the invention herein chosen for the purpose of illustration which do not constitute a departure from the spirit and scope of the invention.

What is claimed is:

1. A scented air delivery device comprising:
   (a) a conduit having two open ends and at least one side opening in a side wall of said conduit;
   (b) a nasal interface affixed to one end of said open ends of said conduit, said nasal interface adapted for wearing in close proximity to a nasal cavity of a user;
   (c) a means for creating an air flow affixed to the other end of said open ends of said conduit, said means for creating an air flow forces air from said other end of said open ends of said conduit to said one end of said two open ends of said conduit and into said nasal interface; and
   (d) a movably insertable means for injecting scent into said air flow through said side opening in said conduit,
   wherein said means for injecting scent moves between a first position within said conduit to inject scent into said air flow and a second position to prevent scent from injecting into said air flow.

2. The device of claim 1 wherein said nasal interface is either a nose mask, a face mask, a tee, a wishbone or an outlet in said conduit.

3. The device of claim 1 wherein said means for creating an air flow in said conduit is a fan or a canister of compressed air.

4. The device of claim 1 wherein the means for injecting scent into said conduit is a plurality of scent reservoirs and said conduit has a plurality of side openings, said reservoirs affixed to the side of said conduit, one at each of said side openings, each reservoir having a means to inject scent into air in said conduit.

5. The device of claim 1 wherein the means for injecting scent into said conduit comprises:
   (a) a frame affixed to said conduit at said side opening;
   (b) a rotatable wheel affixed to said frame, said wheel having an axis of rotation parallel to an axis of said conduit;
   (c) one or more scent containers affixed to said wheel, each of said containers having
      (i) an outer elongated sleeve affixed to said wheel, one end of said outer sleeve being open and adjacent to a rim of said wheel, another end of said outer sleeve facing said axis of said wheel,
      (ii) a scent reservoir having an outlet,
      (iii) an inner sleeve concentric with, positioned in, and movable in said outer sleeve, one end of said inner sleeve being closed and facing said rim of said wheel, another end of said inner sleeve extending into said reservoir through said outlet of said reservoir and affixed to said reservoir at said outlet,
      (iv) at least one window in a side wall of said inner sleeve, said window positioned adjacent said one end of said inner sleeve, and
      (v) a wick positioned in said inner sleeve and extending from said scent reservoir to said window, and
   (d) a motor for rotating said wheel to align each of said inner sleeve of said scent containers with said side opening to allow scent from said scent reservoir to be delivered to an air flow in said conduit,
   wherein said inner sleeve and said reservoir are moved to open and close said window such that, when said window is opened at said first position, said inner sleeve is in said conduit and said window allows scent from said wick to enter said air flow in said conduit and when said window is closed at said second position, said inner sleeve is outside said conduit and said window is against an inside wall of said outer sleeve so as to prevent scent from entering said air flow.

6. The system of claim 5 wherein said means for moving said inner sleeve is a solenoid, a source of electricity, and a spring wherein the source of electricity drives the solenoid to force said inner sleeve upward into said conduit thereby opening the window, and the spring pulls the inner sleeve back into said outer sleeve thereby closing the window when the source of electricity is turned off.

7. The system of claim 5 wherein said means for moving the inner sleeve is a cam and a spring, the cam for opening the window and the spring for closing the window.

8. The system of claim 5 wherein said means for moving said inner sleeve is a motor with eccentric gear that operates on the inner sleeve of each of said scent containers to open said window when said scent containers are aligned with said inlet and a spring which closes said window.

9. A scented air delivery device comprising:
   (a) a conduit having two open ends;
   (b) a nasal interface affixed to one end of said open ends of said conduit, said nasal interface adapted for wearing in close proximity to a nasal cavity of a user;
   (c) a means for creating an air flow affixed to the other end of said open ends of said conduit, said means for creating an air flow forces air from said other end of said open ends of said conduit to said one end of said two open ends of said conduit and into said nasal interface; and
   (d) a plurality of reservoirs each having a liftable cap consecutively positioned within said conduit, along said side wall of said conduit, so as to inject scent into said air flow in said conduit,
   wherein said liftable cap moves between a first position within said conduit to inject scent into said air flow and a second position to prevent scent from injecting into said air flow.

10. The device of claim 9 wherein said nasal interface is either a nose mask, a face mask, a tee, a wishbone or an outlet in said conduit.

11. The device of claim 9 wherein said means for creating an air flow in said conduit is a fan or a canister of compressed air.

12. The device of claim 9 wherein said reservoirs are affixed to the side of said conduit below a corresponding cap.

13. The device of claim 9 further comprising an electrically active dynamic alloy wire attached to said cap to move said cap to said first position when said wire is activated and a coil spring attached to said cap to move said cap to said second position when said wire is deactivated.

* * * * *